US012601542B2

(12) United States Patent (10) Patent No.: US 12,601,542 B2
Butzler et al. (45) Date of Patent: Apr. 14, 2026

(54) LYOPHILIZED REAGENTS

(71) Applicants: Northwestern University, Evanston, IL (US); MINUTE MOLECULAR DIAGNOSTICS, INC., Evanston, IL (US)

(72) Inventors: Matthew A. Butzler, Arlington Heights, IL (US); Jennifer L. Reed, Chicago, IL (US); Sally McFall, Evanston, IL (US); Abhishek K. Agarwal, Evanston, IL (US); David M. Kelso, Wilmette, IL (US); Tom Westberg, Lake Forest, IL (US)

(73) Assignees: Northwestern University, Evanston, IL (US); Nuclein, LLC, Austin, TX (US)

( * ) Notice: Subject to any disclaimer, the term of this patent is extended or adjusted under 35 U.S.C. 154(b) by 823 days.

(21) Appl. No.: 17/785,461

(22) PCT Filed: Dec. 15, 2020

(86) PCT No.: PCT/US2020/065012
§ 371 (c)(1),
(2) Date: Jun. 15, 2022

(87) PCT Pub. No.: WO2021/126801
PCT Pub. Date: Jun. 24, 2021

(65) Prior Publication Data
US 2023/0138093 A1 May 4, 2023

Related U.S. Application Data

(60) Provisional application No. 62/948,643, filed on Dec. 16, 2019.

(51) Int. Cl.
*F26B 5/06* (2006.01)
*A61K 9/16* (2006.01)
(Continued)

(52) U.S. Cl.
CPC .................. *F26B 5/06* (2013.01); *A61K 9/16* (2013.01); *A61K 9/19* (2013.01); *F25D 31/00* (2013.01); *G01N 1/42* (2013.01)

(58) Field of Classification Search
CPC .. F26B 5/06; F25D 31/00; G01N 1/42; A61K 9/16; A61K 9/19
(Continued)

(56) References Cited

U.S. PATENT DOCUMENTS 2,491,837 A    12/1949  Smith-Johannsen et al.
5,689,895 A  *  11/1997  Sutherland ................ F26B 5/06
                                                        215/310
(Continued)

FOREIGN PATENT DOCUMENTS

CN        114401712  B  *  7/2024   ............. A61K 39/00
EP          4078055  B1  *  3/2025   ............... G01N 1/42
(Continued)

OTHER PUBLICATIONS

European Partial Supplementary Search Report for Application No. 20901060.2 dated Nov. 20, 2023 (14 pages).
(Continued)

*Primary Examiner* — Stephen M Gravini
(74) *Attorney, Agent, or Firm* — David W. Staple; Casimir Jones, S.C.

(57) ABSTRACT

Provided herein are methods of producing lyophilized reagents with desired physical characteristics, and the lyophilized reagents produced thereby. In particular, lyophilized combinations of reagents are provided with specific physical geometries that provide optimized use in assays and devices.

4 Claims, 12 Drawing Sheets

MOVEABLE STOPPER WITH VENT SLOT
COVER
O-RING
ALUMINUM BASE

(51) Int. Cl.
　　*A61K 9/19* 　　　　(2006.01)
　　*F25D 31/00* 　　　(2006.01)
　　*G01N 1/42* 　　　 (2006.01)

(58) Field of Classification Search
　　USPC ........................................................ 34/296
　　See application file for complete search history.

(56) References Cited

U.S. PATENT DOCUMENTS

| | | | | |
|---|---|---|---|---|
| 9,417,166 | B2 * | 8/2016 | Thorne | A01N 1/145 |
| 9,863,699 | B2 * | 1/2018 | Corbin, III | A61M 1/0272 |
| 11,047,620 | B2 * | 6/2021 | Beutler | F26B 21/003 |
| 11,433,023 | B2 * | 9/2022 | Markovic | A61K 33/24 |
| 11,673,134 | B2 | 6/2023 | Kelso et al. | |
| 11,957,790 | B1 * | 4/2024 | Harkins, Jr. | A61K 9/19 |
| 12,109,311 | B2 * | 10/2024 | Slocum | A61K 9/19 |
| 12,225,914 | B1 * | 2/2025 | Porter | F26B 25/063 |
| 2007/0259348 | A1 | 11/2007 | Phadke et al. | |
| 2009/0133410 | A1 * | 5/2009 | Thorne | A01N 1/10 |
| | | | | 62/51.1 |
| 2011/0256231 | A1 | 10/2011 | Lin et al. | |
| 2012/0048764 | A1 | 3/2012 | Middelbeek et al. | |
| 2014/0017318 | A1 | 1/2014 | O'Connell et al. | |
| 2014/0294872 | A1 | 10/2014 | Barr et al. | |
| 2018/0098977 | A1 * | 4/2018 | Yaman | A61P 25/00 |
| 2018/0311172 | A1 | 11/2018 | Bhambhani et al. | |
| 2020/0171503 | A1 | 6/2020 | Mcfall et al. | |
| 2023/0138093 | A1 * | 5/2023 | Butzler | F25D 31/00 |
| | | | | 34/296 |
| 2023/0312700 | A1 * | 10/2023 | Jones | A61K 38/13 |
| | | | | 424/158.1 |
| 2024/0139169 | A1 * | 5/2024 | De Vivo | A61K 31/4174 |

FOREIGN PATENT DOCUMENTS

| | | | | |
|---|---|---|---|---|
| JP | 2008-174505 | 7/2008 | | |
| WO | WO-2021126801 | A1 * | 6/2021 | G01N 1/42 |

OTHER PUBLICATIONS

International Search Report and Written Opinion for PCT/US2020/065012. Mailed Mar. 23, 2021. 10 pages.

Ramakers et al., Assumption-free analysis of quantitative real-time polymerase chain reaction (PCR) data. Neurosci Lett. Mar. 13, 2003;339(1):62-6.

Ruijter et al., Amplification efficiency: linking baseline and bias in the analysis of quantitative PCR data. Nucleic Acids Res. Apr. 2009;37(6):e45. 12 pages.

Office Action for CN 202080087262.x. Issued Jul. 31, 2023. 28 pages.

* cited by examiner

PLATE WITH PROTRUSIONS

PLATE WITH DEPRESSIONS

MOVEABLE STOPPER
WITH VENT SLOT

COVER

O-RING

ALUMINUM
BASE

ASSEMBLY CROSS SECTION

VENT CAP IN OPEN POSITION

VENT CAP IN CLOSED POSITION

PLATES IN LYO-SAUCER

| Dextran (w/v in 4.4uL lyo mix) | | | | | | | | | | |
|---|---|---|---|---|---|---|---|---|---|---|
| | 1% | 2% | 3% | 4% | 5% | 6% | 7% | 8% | 9% | 10% |
| Coin Solubility | | | | | | | | | | |
| Coin Durability | | | | | | | | | | |
| PCR Tolerance | | | | | | | | | | |

Acceptable range (for protrusion method)

| Trehalose (w/v in 4.4uL lyo mix) | | | | | | |
|---|---|---|---|---|---|---|
| 12% | 13% | 14% | 15% | 16% | 17% | 18% |
| | | | | | | |
| | | | | | | |
| | | | | | | |

Acceptable range (for protrusion method)

FIG. 7

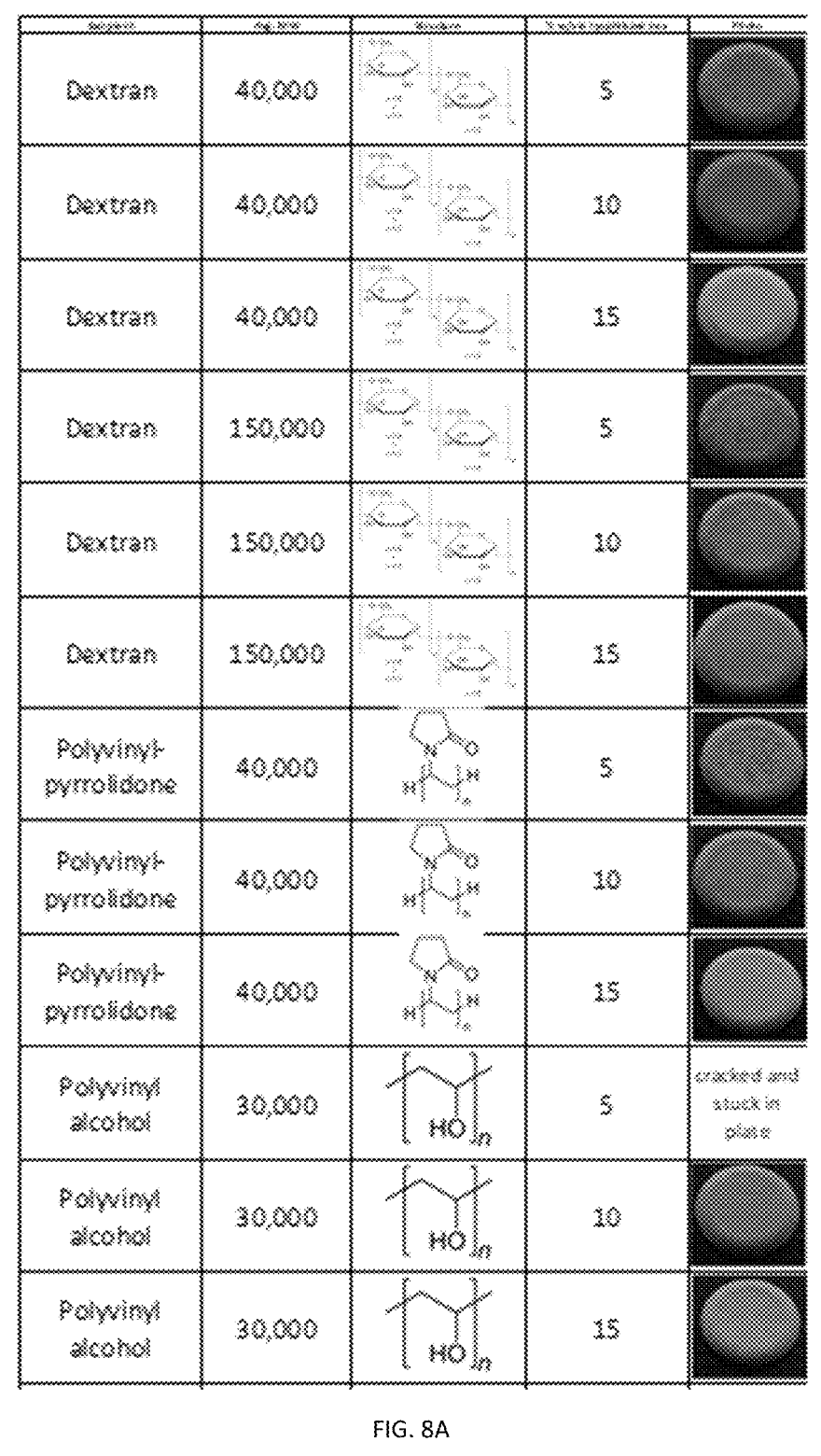

| Polymer | MW, DPN | Structure | % solid composition (w/v) | Film |
|---|---|---|---|---|
| Dextran | 40,000 | | 5 | |
| Dextran | 40,000 | | 10 | |
| Dextran | 40,000 | | 15 | |
| Dextran | 150,000 | | 5 | |
| Dextran | 150,000 | | 10 | |
| Dextran | 150,000 | | 15 | |
| Polyvinyl-pyrrolidone | 40,000 | | 5 | |
| Polyvinyl-pyrrolidone | 40,000 | | 10 | |
| Polyvinyl-pyrrolidone | 40,000 | | 15 | |
| Polyvinyl alcohol | 30,000 | | 5 | cracked and stuck in plate |
| Polyvinyl alcohol | 30,000 | | 10 | |
| Polyvinyl alcohol | 30,000 | | 15 | |

FIG. 8A

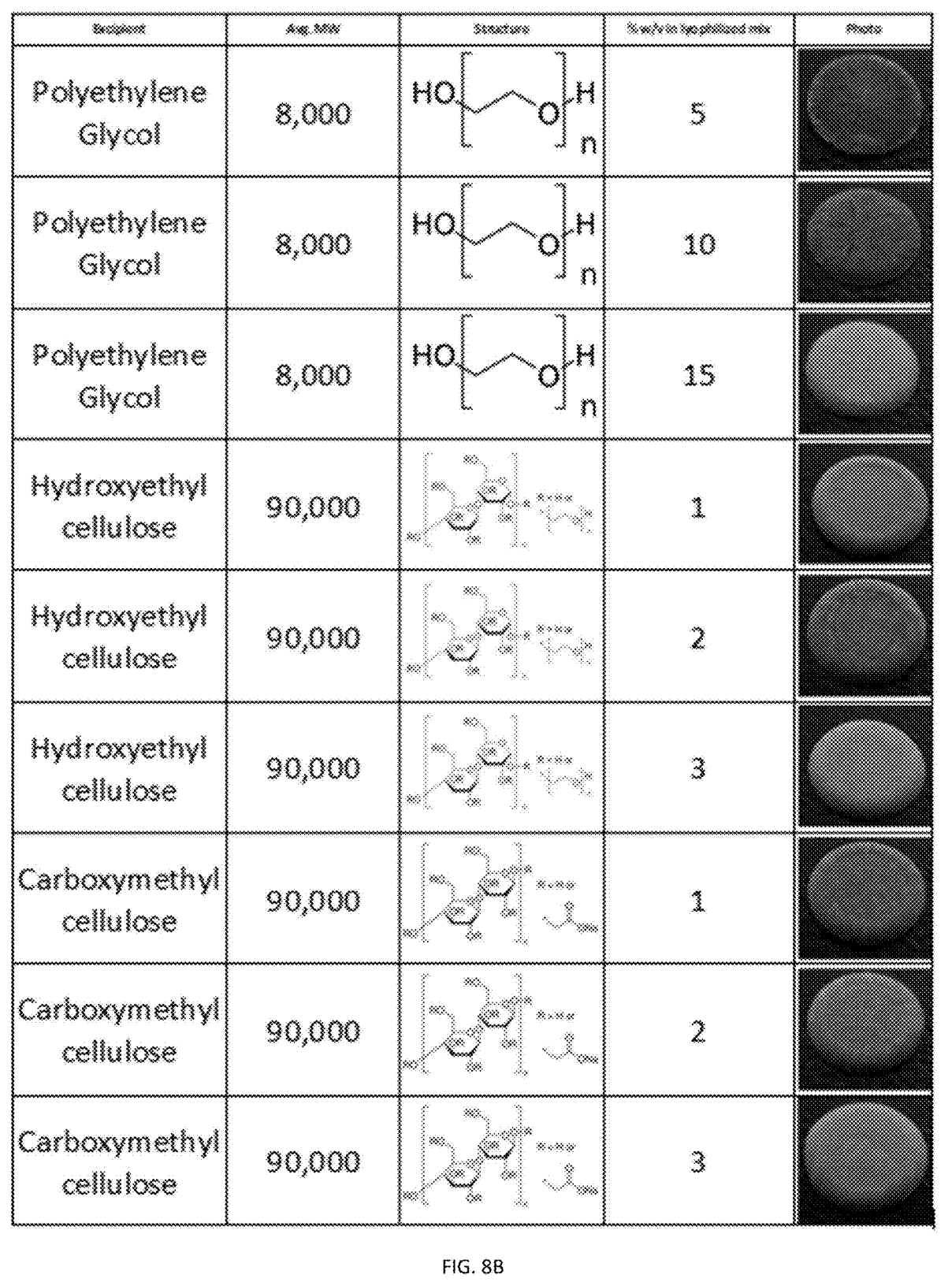

| Excipient | Avg. MW | Structure | % w/v in lyophilized mix | Photo |
|---|---|---|---|---|
| Polyethylene Glycol | 8,000 | | 5 | |
| Polyethylene Glycol | 8,000 | | 10 | |
| Polyethylene Glycol | 8,000 | | 15 | |
| Hydroxyethyl cellulose | 90,000 | | 1 | |
| Hydroxyethyl cellulose | 90,000 | | 2 | |
| Hydroxyethyl cellulose | 90,000 | | 3 | |
| Carboxymethyl cellulose | 90,000 | | 1 | |
| Carboxymethyl cellulose | 90,000 | | 2 | |
| Carboxymethyl cellulose | 90,000 | | 3 | |

FIG. 8B

LYOPHILIZED REAGENTS

RELATED APPLICATIONS

This application is a national phase application under 35 U.S.C. § 371 of PCT International Application No.: PCT/US2020/065012, filed on Dec. 15, 2020, which claims priority to U.S. Provisional Patent Application No. 62/948,643, filed Dec. 16, 2019, the entire contents of which are incorporated herein by reference.

FIELD

Provided herein are methods of producing lyophilized reagents with desired physical characteristics, and the lyophilized reagents produced thereby. In particular, lyophilized combinations of reagents are provided with specific physical geometries that provide optimized use in assays and devices.

BACKGROUND

Pipetting of reagents during laboratory methods such as polymerase chain reaction (PCR) introduces the potential for error, and therefore increases the risk of decreased accuracy of results. Accordingly, methods using pre-measured amounts of lyophilized reagents would be beneficial. However, methods for forming lyophilized reagents must optimize various factors, including the size, shape, durability, and solubility of the lyophilized product while also enabling the product to function properly in the desired assay. Accordingly, novel methods for forming lyophilized reagents with particular physical characteristics are needed.

SUMMARY

Provided herein are methods for producing lyophilized reagents with desired physical characteristics, and the lyophilized reagents produced thereby.

In some aspects, provided herein are methods for forming a circular pellet with a planar bottom and a domed top. In some embodiments, the methods comprise placing a single droplet of a reagent mixture onto a planar surface that is chilled to a temperature below the freezing temperature of the reagent mixture such that the single droplet freezes upon contact with the planar surface.

In some embodiments, the method for forming a circular pellet with a planar bottom and a domed top comprises placing a volume of a reagent mixture onto a planar-topped column such that the volume of the reagent mixture spreads to the edges of the planar-topped column, freezing the reagent mixture atop the planar-topped column, and lyophilizing the reagent mixture atop the planar-topped column to form a pellet that approximates the shape of the perimeter of the column with a planar bottom and a planar top.

In some aspects, provided herein are methods for forming a circular pellet with a planar bottom and a planar top. In some embodiments, the method comprises placing a volume of a reagent mixture into a well such that the volume of the reagent mixture completely fills the well the well, freezing the reagent mixture within the well, and lyophilizing the reagent mixture within the well to form a pellet that approximates the shape of the perimeter of the well with a planar bottom and a planar top.

In some aspects, the disclosure provides lyophilized pellets made by any of the methods described herein.

BRIEF DESCRIPTION OF THE DRAWINGS

FIG. 7 is a table showing selection of appropriate dextran and trehalose amounts.

FIG. 8A-8B show test results for potential excipients and concentrations thereof in the formation of lyophilized pellets by methods described herein. Pellets were considered acceptable if they could be removed from depression plate with a vacuum pen without breaking apart.

DEFINITIONS

Figure 1A:
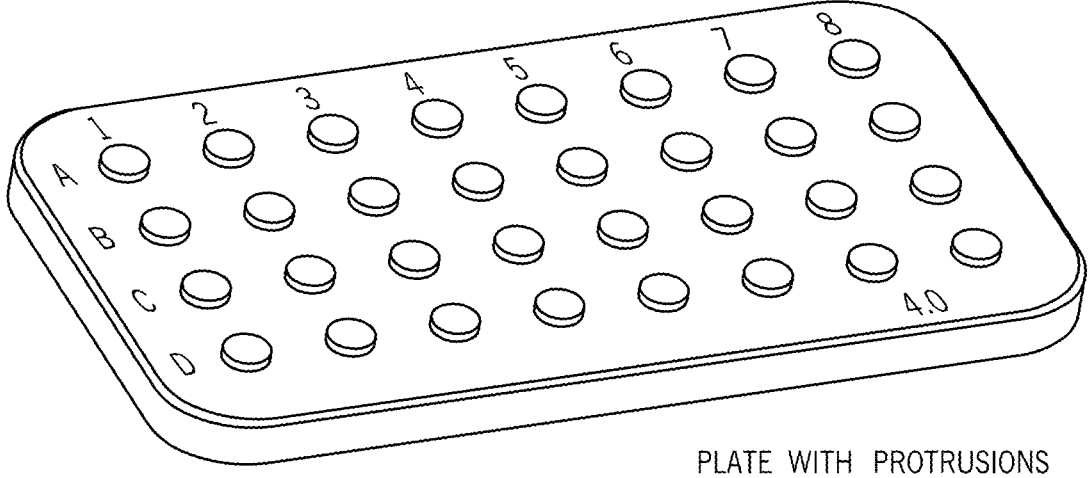
FIG. 1A shows an exemplary plate containing multiple planar-topped columns (e.g. protrusions).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a widget" can mean one widget or a plurality of widgets.

As used herein, the term "about," when referring to a value is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

DETAILED DESCRIPTION

In some embodiments, provided herein are methods for producing lyophilized reagents with desired physical characteristics. In some embodiments, the lyophilized reagent comprises a particular desired physical shape. In some embodiments, the desired shape is a circular pellet with a planar bottom and a domed top. In some embodiments, provided herein are methods for forming a circular pellet with a planar bottom and a domed top, comprising placing a single droplet of a reagent mixture onto a planar surface that is chilled to a temperature below the freezing temperature of the reagent mixture such that the single droplet freezes upon contact with the planar surface. In some embodiments, the method may be used to form a pellet having a thickness of about 1 mm or greater. For example, the pellet formed by this method may have a thickness of 1 mm, 1.1 mm, 1.2 mm, 1.3 mm, 1.4 mm, 1.5 mm, 1.6 mm, 1.7 mm, 1.8 mm, 1.9 mm, 2.0 mm, or greater.

In some embodiments, the method may be used to form a single pellet or multiple pellets. For methods of forming multiple pellets, a plate containing multiple planar surfaces may be used. For example, a plate containing an array of planar surfaces may be used.

In some embodiments, the planar surface comprises a metallic surface. For example, the planar surface may comprise an aluminum surface. In some embodiments, the planar surface comprises a glass surface.

In some embodiments, the planar surface is chilled to a temperature below the freezing point of the reagent mixture. In some embodiments, the planar surface is chilled to a temperature below −5° C. For example, the planar surface may be chilled to a temperature below −5° C., below −10° C., below −20° C., below −30° C., below −40° C., below −50° C., below −60° C., etc. In some embodiments, the planar surface is chilled to a temperature below −25° C. In some embodiments, the planar surface is chilled to a temperature of about −50° C.

Chilling the planar surface to a temperature below the freezing point of the reagent mixture allows the reagent mixture to freeze upon contact with the planar surface. The term "upon contact" refers to freezing within 1 second of contact with the planar surface. For example, the droplet may freeze within 1 second of contact with the planar surface. In some embodiments, the droplet freezes within 100 milliseconds of contact with the planar surface. For example, the droplet may freeze within 100 milliseconds, 10 milliseconds, 1 millisecond, 100 microseconds, 10 microseconds, or 1 microsecond of contact with the planar surface.

In some embodiments, the droplet is placed onto the planar surface by a pipette. For example, the droplet may be placed onto the planar surface by holding the pipette above the planar surface with the tip at a non-90° angle with respect to the planar surface, dispensing a droplet of the reagent mixture from the pipette such that the droplet clings to the tip of the pipette, and rotating the pipette to a vertical position such that the droplet falls from the tip to the planar surface. The pipette may be held any suitable distance above the planar surface while the reagent mixture is dispensed. Suitable distances include, for example, 0.5-4 inches. For example, the pipette may be held such that the bottom opening of the pipette tip (e.g. the bore from which the droplet will be released) is 0.5-4 inches above the planar surface. For example, the pipette may be held such that the bottom opening of the pipette tip is about 0.5, 1, 1.5, 2, 2.5, or 3 inches above the planar surface. The non-90° angle with respect to the planar surface may be any suitable angle between 90° (e.g. completely vertical, perpendicular to the planar surface) and 0° (e.g. parallel to the planar surface). For example, the pipette may be held at an angle (with respect to the planar surface) of about 0-80°, 5-75°, 10-70°, 15-65°, 20-60°, 25-55°, 30-50°, or 35-45°. In some embodiments, the pipette is held at an angle of about 0°, 5°, 10°, 15°, 20°, 25°, 30°, 35°, 40°, 45°, 50°, 55°, 60°, 65°, 70°, 75°, 80°, or 85° relative to the planar surface while the droplet of reagent mixture is dispensed such that the droplet clings to the pipette. Subsequently, the pipette may be rotated such that the droplet falls from the tip onto the planar surface. In some embodiments, placing the droplet on the planar surface is performed manually. In other embodiments, droplet placement on the planar surface is at least partially automated. For example, a pipette may be operably connected to a device which operates the one or more functions of the pipette. For example, the device may facilitate movement of the pipette and/or facilitate aspirating and dispensing of the contents held within a pipette tip attached thereto.

In some embodiments, the method further comprises removing the pellet from the planar surface after the pellet freezes. The pellet may be removed by any suitable means. In some embodiments, the pellet is removed from the planar surface by use of a suitable tool. For example, the pellet may be removed by using a scraping instrument, such as a razor blade. In some embodiments, the tool is chilled. The tool may be chilled to a suitable temperature such that touching the pellet with the tool does not thaw (partially or completely) the pellet. In some embodiments, the tool is chilled to a temperature above the freezing point of the pellet. For example, the tool may be chilled to a temperature between −5° C. and 15° C. In other embodiments, the tool is chilled to a temperature below the freezing point of the pellet. For example, the tool may be chilled to a temperature below −5° C. (e.g. below −5° C., below −10° C., below −20° C., below −30° C., below −40° C., below −50° C., below −60° C., etc.)

In some embodiments, the pellet is transferred to a container after removal of the pellet from the planar surface. The container may be a container suitable for lyophilization. The container may be chilled. For example, the container may be chilled to a suitable temperature such that the pellet does not thaw (partially or completely) upon contact with the container. In some embodiments, the container is chilled to a temperature above the freezing point of the pellet. For example, the container may be chilled to a temperature between −5° C. and 15° C. In other embodiments, the container is chilled to a temperature below the freezing point of the pellet. For example, the container may be chilled to a temperature below −5° C. (e.g. below −5° C., below −10° C., below −20° C., below −30° C., below −40° C., below −50° C., below −60° C., etc.).

In some embodiments, the pellet is lyophilized. For example, the pellet may be lyophilized after removal from the planar surface. In some embodiments, the pellet is lyophilized within the container. The container may be any suitable container for lyophilization, such as a glass container. For example, the pellet may be lyophilized within a glass vial and then sealed to complete the vacuum and prevent lyophilized pellets from being exposed to the ambient environment. In some embodiments, the container contains multiple pellets to be lyophilized. The pellets within the container may be lyophilized by any suitable means as known in the art.

Other suitable methods for forming a pellet having a planar bottom and a domed top are additionally described herein. In some embodiments, provided herein is a method for forming a circular pellet having a planar bottom and a domed top, comprising placing a volume of a reagent mixture onto a planar-topped column (e.g. a protrusion) such that the volume of the reagent mixture spreads to the edges of the planar-topped column, freezing the reagent mixture atop the planar-topped column, and lyophilizing the reagent mixture atop the planar-topped column to form a pellet that approximates the shape of the perimeter of the column with a planar bottom and a planar top. Such methods may be used to form a thin pellet, having a thickness less than 1 mm. For example, the thickness of the pellet may be 900 μm, 800 μm, 700 μm, 600 μm, 500 μm, 400 μm, 300 μm, 200 μm, 100 μm, 90 μm, 80 μm, 70 μm, 60 μm, 50 μm, 40 μm, 30 μm, 20 μm, 10 μm, 1 μm, or less. This thin pellet thus enables efficient, rapid heat transfer, such as during PCR.

In some embodiments, the method may be used to form a single pellet or multiple pellets. For methods of forming multiple pellets, a plate containing multiple planar-topped columns may be used. For example, a plate containing an array of planar-topped columns may be used.

In some embodiments, the planar-topped column comprises a circular top cross-section. In some embodiments, the planar-topped column comprises circular top cross-section having a diameter of 2-10 mm. For example, the diameter may be 2 mm, 3 mm, 4 mm, 5 mm, 6 mm, 7 mm, 8 mm, 9 mm, or 10 mm. For example, the diameter may be 4-6 mm. Accordingly, the diameter of the final lyophilized pellet with a planar bottom and a planar may be 2-10 mm. For example, the diameter of the pellet may be 2 mm, 3 mm, 4 mm, 5 mm, 6 mm, 7 mm, 8 mm, 9 mm, or 10 mm. In some embodiments, the diameter may be marginally reduced during lyophilization. For example, the presence of dextran in the reagent mixture may cause the diameter of the pellet to be reduced about 5-15% during lyophilization.

In some embodiments, the planar-topped column comprises a metallic surface. For example, the planar-topped column may comprise an aluminum surface. In some embodiments, the planar-topped column comprises a glass surface.

In some embodiments, the planar-topped column is coated with a hydrophilic coating. Any suitable hydrophilic coating may be used. In some embodiments, a hydrophilic coating that does not interfere with subsequent use of the lyophilized pellet in PCR may be used. For example, the hydrophilic coating may be Hendlex Antifog (Baltic Nanotechnologies).

In some embodiments, the planar-topped column is chilled to a temperature above the freezing point of the reagent mixture such that the volume of the reagent mixture spreads to the edges of the planar-topped column (i.e., the mixture does not freeze upon contact with the planar-topped column). For example, the planar-topped column may be chilled to a temperature between −5° C. and 15° C. For example, the planar-topped column may be chilled to a temperature of −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., or 15° C.

In some embodiments, the volume of the reagent mixture is placed onto the planar-topped column by a pipette. In some embodiments, the volume of the reagent mixture is placed onto the planar-topped column manually. In other embodiments, droplet placement on the planar-topped column is at least partially automated. For example, a pipette may be operably connected to a device which operates the one or more functions of the pipette. For example, the device may facilitate movement of the pipette and/or facilitate aspirating and dispensing of the contents held within a pipette tip attached thereto.

In some embodiments, the volume of the reagent mixture placed atop the planar-topped column is 1 μl to 20 μl. For example, the volume of the reagent mixture may be about 1 μl, about 2 μl, about 3 μl, about 4 μl, about 5 μl, about 6 μl, about 7 μl, about 8 μl, about 9 μl, about 10 μl, about 11 μl, about 12 μl, about 13 μl, about 14 μl, about 15 μl, about 16 μl, about 17 μl, about 18 μl, about 19 μl, or about 20 μl. The volume may depend on the diameter of the planar-topped column and/or the intended size of the lyophilized pellet.

The method further comprises freezing the reagent mixture atop the planar-topped column prior to lyophilization. For example, the reagent mixture may be frozen prior to lyophilization by application of liquid nitrogen. Alternatively, the reagent mixture may be frozen by exposing the planar-topped column containing the reagent mixture to an environment chilled to a temperature below the freezing point of reagent mixture. For example, the reagent mixture may be frozen atop the planar-topped column by exposing the planar-topped column to an environment chilled to a temperature of below −5° C. For example, environment may be chilled to a temperature of below −5° C., below −10° C., below −20° C., below −30° C., below −40° C., below −50° C., or below −60° C.

After freezing the reagent mixture, the frozen mixture is lyophilized atop the planar-topped column. Lyophilization may be performed using a specialized device (e.g. "lyosaucer") described herein for lyophilizing atop the planar-topped column. In some embodiments, lyophilization occurs by transferring the planar-topped column containing the frozen pellet to a freeze dryer chilled to a temperature below the freezing point of the reagent mixture. For example, the freeze dryer may be chilled to a temperature below −5° C. For example, the freeze dryer may be chilled to a temperature below −5° C., below −10° C., below −20° C., below −30° C., below −40° C., below −50° C., or below −60° C., under suitable conditions for lyophilization to occur. In some embodiments, the freeze dryer is chilled to −55° C.

In some embodiments, the method further comprises removing the pellet from the planar surface after lyophilization. The pellet may be removed from the planar surface using any suitable tool. For example, the pellet may be removed using a vacuum pen. The pellet may be transferred to a suitable container following removal from the planar surface. For example, the pellet may be transferred to a chilled container. In some embodiments, the pellet is transferred into a suitable cartridge for subsequent use in PCR.

In some embodiments, the desired shape of the lyophilized agent is a circular pellet with a planar bottom and a planar top (e.g., a "disk"). In some embodiments, provided herein are methods forming a circular pellet with a planar bottom and a planar top. In some embodiments, methods for producing a circular pellet with a planar bottom and a planar top comprise placing a volume of a reagent mixture into a well. In some embodiments, provided herein are methods for producing a circular pellet with a planar bottom and a planar top comprising placing a volume of a reagent mixture into a well, freezing the reagent mixture within the well, and lyophilizing the reagent mixture within the well to form a pellet that approximates the shape of the perimeter of the well with a planar bottom and a planar top.

In some embodiments, the method may be used to form a single pellet or multiple pellets. For methods of forming multiple pellets, a plate containing multiple wells may be used. For example, a plate containing an array of wells may be used.

In some embodiments, the well is cylindrical in shape having a circular top cross section and a circular bottom cross section. In some embodiments, the diameter of the circular top cross section is the same as the diameter of the circular bottom cross section. In other embodiments, the diameter of the circular top cross is greater than the diameter of the circular bottom cross section.

The diameter of the circular top cross section and the diameter of the circular bottom cross section may be any suitable diameter, depending on the intended size of the circular pellet to be produced. In some embodiments, the diameter of the circular top cross section is 1 mm to 10 mm. For example, the diameter of the circular top cross section may be about 1 mm, about 2 mm, about 3 mm, about 4 mm, about 5 mm, about 6 mm, about 7 mm, about 8 mm, about 9 mm, or about 10 mm. In some embodiments, the diameter of the circular bottom cross section is 1 mm to 10 mm. For example, the diameter of the circular bottom cross section may be about 1 mm, about 2 mm, about 3 mm, about 4 mm, about 5 mm, about 6 mm, about 7 mm, about 8 mm, about 9 mm, or about 10 mm. In some embodiments, the diameter of the circular top cross section is about 4 mm and the diameter of the circular bottom cross section is about 3 mm.

Any suitable volume of reagent mixture may be loaded into the well, depending on the size of the well and the intended size of the pellet to be produced. In some embodiments, the volume of the reagent mixture and the size of the well are selected to allow for expansion and subsequent freezing of the pellet without the formation of a convex meniscus. In some embodiments, the volume of the reagent mixture and the size of the well are selected such that the reagent mixture fills the well completely. In some embodiments, the volume of reagent mixture is 3 µl to 6 µl. For example, the volume may be about 3 µl, about 4 µl, about 5 µl, or about 6 µl. For example, the volume may be 3.1 µl, 3.2 µl, 3.3 µl, 3.4 µl, 3.5 µl, 3.6 µl, 3.7 µl, 3.8 µl, 3.9 µl, 4.0 µl, 4.1 µl, 4.2 µl, 4.3 µl, 4.4 µl, 4.5 µl, 4.6 µl, 4.7 µl, 4.8 µl, 4.9 µl, 5.0 µl, 5.1 µl, 5.2 µl, 5.3 µl, 5.4 µl, 5.5 µl, 5.6 µl, 5.7 µl, 5.8 µl, 5.9 µl, or 6.0 µl. In particular embodiments, the volume of the reagent mixture is 4.4 µl.

In some embodiments, the well is chilled to a temperature above the freezing point of the reagent mixture such that the volume of the reagent mixture spreads to the edges of the well. For example, the well may be chilled to a temperature of about −5° C. to about 15° C. For example, the well may be chilled to a temperature of −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., or 15° C.

In some embodiments, the well comprises a metallic surface. For example, the well may comprise an aluminum surface. In some embodiments, the well comprises a glass surface.

In some embodiments, the well is coated with a hydrophilic coating. Any suitable hydrophilic coating may be used. In some embodiments, a hydrophilic coating that does not interfere with subsequent use of the lyophilized pellet in PCR may be used. For example, the hydrophilic coating may be Hendlex Antifog (Baltic Nanotechnologies).

In some embodiments, the volume of the reagent mixture is placed into the well by a pipette. The pipette may be operated manually.

The method comprises freezing the reagent mixture within the well prior to lyophilization. The reagent mixture may be frozen by any suitable means, including application of liquid nitrogen to the well or exposing the well to an environment chilled to a temperature below the freezing point of the reagent mixture. For example, the reagent mixture may be frozen within the well by exposing the well to an environment chilled to a temperature of below −5° C. For example, the reagent mixture may be frozen within the well by exposing to an environment chilled to a temperature of below −5° C., below −10° C., below −20° C., below −30° C., below −40° C., below −50° C., or below −60° C. In some embodiments, the reagent mixture is frozen at −45° C.

The method further comprises lyophilizing the reagent mixture after freezing to form the circular pellet with a planar bottom and a planar top (e.g., the disk). The reagent mixture is lyophilized within the well. The reagent mixture may be lyophilized within the well using a specialized device for lyophilization (e.g. "lyo-saucer"), described herein.

In some embodiments, the method further comprises removing the pellet from the well after lyophilization. For example, the pellet may be removed using a vacuum pen. The pellet may be stored in a suitable container following removal from the well. For example, the pellet may be stored in a chilled container.

Lyophilized products are typically prepared in glass vials sealed with rubber stoppers that are sealed inside the lyophilizer after the freeze dry process is complete and before breaking vacuum so that the product is not exposed to the room's humidity. However, to make the pellets using the planar-topped columns or wells disclosed herein a different container-closure system for lyophilization is needed. The container-disclosure system developed is referred to herein as the "lyo-saucer". The lyo-saucer comprises a metallic base plate with a cover, and a means for creating a seal between the base plate and the cover. For example, the lyo-saucer may comprise an aluminum base plate, which provides thermal conductivity. The cover may be an acrylic or polycarbonate cover to allow for transparency. Alternatively, the cover may comprise other suitable plastics or metals. The cover may further comprise one or more movable stoppers with a vent. In some embodiments, the lyo-saucer further comprises a ring, which creates the seal between the cover and the base plate. The seal between the cover and the aluminum base may be created by an O-ring or quad ring seal. During the lyophilization process the vent cap will initially be in the open position and at the end of the process a vacuum is drawn to evacuate the chamber, and the vent cap is pushed down to seal off the chamber. Exemplary drawings of the lyo-saucer device described herein are shown in FIGS. 3A-3E.

For any of the methods described herein, any one or more steps may be performed manually. For example, the reagent mixture may be placed onto the desired surface (e.g. well, planar-topped column, planar surface) manually using a pipette, removed from the surface manually using a suitable tool (e.g. razor blade, vacuum pen), transferred into a container manually using a suitable tool, etc. For any of the methods described herein, any one or more steps may be at least partially automated. For example, the reagent mixture may be placed onto the desired surface using a pipette that is operably connected to a device that controls the movement of the pipette. For example, the device may control one or more aspects of pipette use, including aspirating the reagent mixture, the angle at which the pipette is held relative to the surface (e.g. the angle relative to the surface of a planar-topped column), forming the droplet of the reagent mixture, and the like.

For any of the methods and embodiments described herein, the reagent mixture may be placed onto the desired surface comprise any suitable reagent. For example, the reagent mixture may comprise PCR reagents. For example, the reagent mixture may comprise any suitable combination of primers, probes, salts, buffers, lysis reagents, bulking agents, binding agents, excipients, labeling agents, particles, DNA, RNA, and the like typically used in PCR assays. In some embodiments, the reagent mixture comprises a combination of one or more of the following: magnetic particles, Proteinase K, $CaCl_2$, HEPES buffer, dNTPs, one or more primers, one or more probes, one or more enzymes (e.g. DNA polymerase, reverse transcriptase), Tween 20 (ThermoFisher), bovine serum albumen, one or more bulking agents, and one or more binding agents. In some embodiments, the pellet comprises lysis reagents, including proteinase K, $CaCl_2$, and HEPES buffer. In some embodiments, the pellet comprises paramagnetic particles. In some embodiments, the pellet comprises dNTPs, one or more primers, one or more probes, and one or more enzymes.

In some embodiments, the lyophilized pellet comprises one or more bulking agents. In general, suitable bulking agents may be used to provide a well-formed pellet with good mechanical properties. Accordingly, one or more bulking agents may be added to provide enough solids to reagent to make a pickable solid reagent and also serve as a stabilizer for lyophilized materials. Common bulking agents include disaccharides such as sucrose, mannitol and trehalose.

In some embodiments, the lyophilized pellet comprises one or more binding agents. Binding agents are long chain hydrophilic polymers that form the lyophilized reagent into a cohesive whole providing structural stability. For example, the binding agent may be dextran, polyvinylpyrrolidone, polyvinylalcohol, polyethylene glycol, hydroxyethylcellulose, carboxymethylcellulose, or a combination thereof. In some embodiments, the lyophilized pellet comprises a binding agent at a concentration of 1-20% (w/v). For example, the lyophilized pellet may comprise a binding agent at a concentration of 1%, 2%, 3%, 4%, 5%, 6%, 7%, 8%, 9%, 10%, 11%, 12%, 13%, 14%, 15%, 16%, 17%, 18%, 19%, or 20%. For example, suitable binding agents and concentrations thereof are provided in (FIGS. 8A-8B).

In some embodiments, the reagent mixture comprises at least one binding agent and at least one bulking agent. In some embodiments, the reagent mixture comprises dextran and trehalose. In some embodiments, the reagent mixture comprises 1-20% dextran. In some embodiments, the reagent mixture comprises 1-10% dextran. For example, the reagent mixture may comprise 1%, 2%, 3%, 4%, 5%, 6%, 7%, 8%, 9%, or 10% dextran. In some embodiments, the reagent mixture comprises 12-18% trehalose. For example, the reagent mixture may comprise 12%, 13%, 14%, 15%, 16%, 17%, or 18% trehalose. In some embodiments, reagent mixture comprises 6-8% dextran and 12-14% trehalose. The reagent mixture may comprise any suitable combination of the above percentages of dextran and trehalose. For example, the reagent mixture may comprise 6% dextran and 12% trehalose, 6% dextran and 13% trehalose, 6% dextran and 14% trehalose, 7% dextran and 12% trehalose, 7% dextran and 13% trehalose, 7% dextran and 14% trehalose, 8% dextran and 12% trehalose, 8% dextran and 13% trehalose, or 8% dextran and 14% trehalose.

In some aspects, provided herein are lyophilized pellets formed by the methods described herein. The lyophilized pellets may be a circular pellet with a planar bottom and a domed top. The lyophilized pellets may be a circular pellet with a planar bottom and a domed top. The lyophilized pellet may be any suitable size, depending on the method used to produce the pellet. For example, the lyophilized pellet may have a diameter of 1 mm to 10 mm. For example, the lyophilized pellet may have a diameter of about 1 mm, about 2 mm, about 3 mm, about 4 mm, about 5 mm, about 6 mm, about 7 mm, about 8 mm, about 9 mm, or about 10 mm. The lyophilized pellet may have a height of about 0.1 mm to about 2 mm. For example, the lyophilized pellet may have a height of about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2.0 mm.

The lyophilized pellet may comprise any suitable mixture of reagents as described herein. For example, lyophilized pellet may comprise PCR reagents. For example, the lyophilized pellet may comprise any suitable one or combination of magnetic particles, Proteinase K, $CaCl_2$, HEPES buffer, dNTPs, one or more primers, one or more probes, one or more enzymes (e.g. DNA polymerase, reverse transcriptase), tween, bovine serum albumen, dextran, and/or trehalose. In some embodiments, the lyophilized pellet comprises dextran and trehalose. In some embodiments, the lyophilized pellet comprises 1-10% dextran. For example, the lyophilized pellet may comprise 1%, 2%, 3%, 4%, 5%, 6%, 7%, 8%, 9%, or 10% dextran. In some embodiments, the lyophilized pellet comprises 12-18% trehalose. For example, the lyophilized pellet may comprise 12%, 13%, 14%, 15%, 16%, 17%, or 18% trehalose. In some embodiments, the lyophilized pellet comprises 6-8% dextran and 12-14% trehalose. The lyophilized pellet may comprise any suitable combination of the above percentages of dextran and trehalose. For example, the lyophilized pellet may comprise 6% dextran and 12% trehalose, 6% dextran and 13% trehalose, 6% dextran and 14% trehalose, 7% dextran and 12% trehalose, 7% dextran and 13% trehalose, 7% dextran and 14% trehalose, 8% dextran and 12% trehalose, 8% dextran and 13% trehalose, or 8% dextran and 14% trehalose.

The lyophilized pellet may be placed into a suitable device for performing PCR. Suitable devices include, for example, those described in U.S. application Ser. Nos. 16/615,630 and 16/618,698, the entire contents of which are incorporated herein by reference. In some embodiments, three separate pellets containing three distinct combinations of reagents may be made by the methods described herein and placed into distinct chambers of a suitable PCR device. For example, one pellet containing lysis reagents (e.g.

Proteinase K, CaCl2, and HEPES buffer), one pellet containing paramagnetic particles (e.g. M270 Streptavidin Dynabeads), and one pellet containing the remaining PCR reagents (e.g. polymerase, nucleotides, oligonucleotides stabilizers, binding agents, bulking agents, etc.) may be made and each placed into a separate chamber. The pellets may be resuspended in a suitable buffer and subsequently be used to perform the desired PCR assay. The resuspension buffers may be the same for each pellet, or may be different for one or more pellets. For example, the pellets may be resuspended in a buffer comprising glycerol, $MgCl_2$ or $MnCl_2$, and a surfactant and subsequent PCR may be performed.

EXAMPLES

Example 1—Circular Pellet with Planar Bottom and Domed Top

This example describes an exemplary method for forming a pellet with a circular bottom and a domed top.

Using dry ice or liquid nitrogen, a smooth plate of aluminum or glass was chilled to approximately –50° C. Holding a pipette at an angle with the tip 1 to 3 inches above the plate, the reagent mixture was dispensed such that the liquid still clung to the tip. After the entire volume was dispensed as one liquid drop clinging to the tip, the pipette was rotated to a vertical position. The liquid dropped off the tip and fell to the chilled plate, freezing upon contact.

By knowing the volume of the liquid to be lyophilized, the geometry of the lyophilized product having a planar bottom and a domed top can be closely estimated. Accordingly, lyophilized products can be tailor-made to fit into a specific chamber, such as a chamber for a PCR reaction.

The frozen pellet had a dome shape with a flat bottom. This process may be repeated to form any desired number of pellets.

The pellets were removed from the cold plate using a chilled razor blade. Other suitable scraping implements may be used as an alternative.

The pellets were transferred to chilled vials with chilled forceps and the vials were placed on dry ice or liquid nitrogen. The vials were transferred to the chilled lyophilizer shelf (–45° C.), stoppers were placed in the vials, lyophilization was performed. After lyophilization, the vials were sealed under nitrogen and the tops were crimped.

Example 2—Additional Methods for Pellet Formation

Two methods were used to form additional pellets: an aluminum pan with milled round depressions (e.g. wells) of defined diameter and height to hold a specific volume and an aluminum block with raised round protrusions (e.g. planar-topped columns) of defined diameter. The wells and planar-topped columns can be treated with compounds that modify the surface energy of the mold to control the wetting or beading of the lyophilized product. For example, a hydrophilic coating may be used to achieve complete spreading of the reagent mixture over the protrusion and therefore allow for a very small thicknesses of the finalized lyophilized product.

By knowing the diameter of the planar-topped columns or wells to be used, and the volume of the liquid to be lyophilized, the geometry of the lyophilized pellet can be closely estimated. Accordingly, lyophilized pellets can be tailor-made to fit into a specific chamber, such as a chamber for a PCR reaction.

Figure 1B:
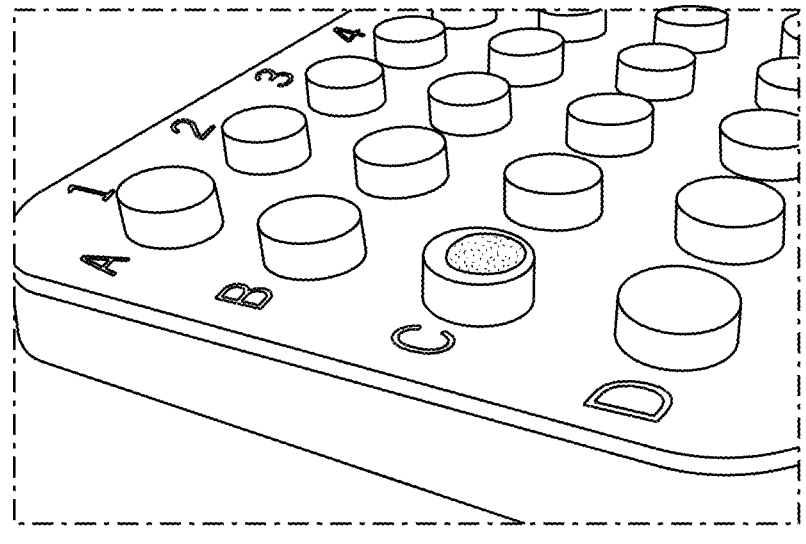
FIG. 1B shows the same plate containing a reagent mixture, wherein one planar-topped column (left) was coated with a hydrophilic coating and the other (right) was not. It can be observed that the pellet benefits from the hydrophilic treatment.

FIG. 1A shows an exemplary plate containing multiple planar-topped columns (e.g. protrusions). FIG. 1B shows the same plate containing a reagent mixture, wherein one planar-topped column (left) was coated with a hydrophilic coating and the other (right) was not. It can be observed that the pellet benefits from the hydrophilic treatment.

Pellet formed on a planar-topped column: In one method, a reagent mixture was freeze dried on an array of aluminum planar-topped columns (e.g. protrusions) coated with hydrophilic coating (in this instance, Hendlex Antifog) to promote wetting of the surface and allow the liquid to spread out to the edges of the column. In this example, the planar-topped column had a circular cross section of 5 mm in diameter. The addition of dextran in the lyophilization mix caused the dried product to shrink to 4.6 mm. However, other suitable diameters may be used.

The reagent mix pipetted onto a chilled plate containing the planar-topped columns. The temperature of the plate was not below the freezing temperature of the reagent mixture. The plate was frozen in liquid nitrogen and transferred to a freeze dryer pre-chilled to –55° C. in the lyo-saucer designed to the hold the protrusion plate and allow sealing in place. After lyophilization, the lyo-saucer was sealed with back filled $N_2$. The lyo-saucer was subsequently opened in the dry room by releasing $N_2$ slowly via piercing stopper with needle. In the dry room, the lyophilized pellets were moved from the plate to a cartridge using a vacuum pen. Adhesive fingers in the PCR chamber were used for placement of the pellet. Unused pellets were stored in tubes sealed in aluminum pouches with desiccant.

Figure 2A:
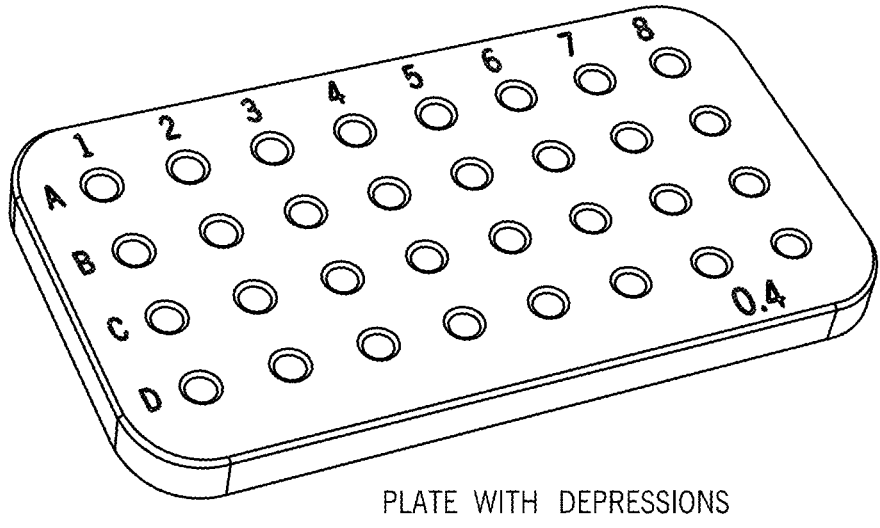
FIG. 2A shows an exemplary plate containing multiple wells.
Figure 2B:
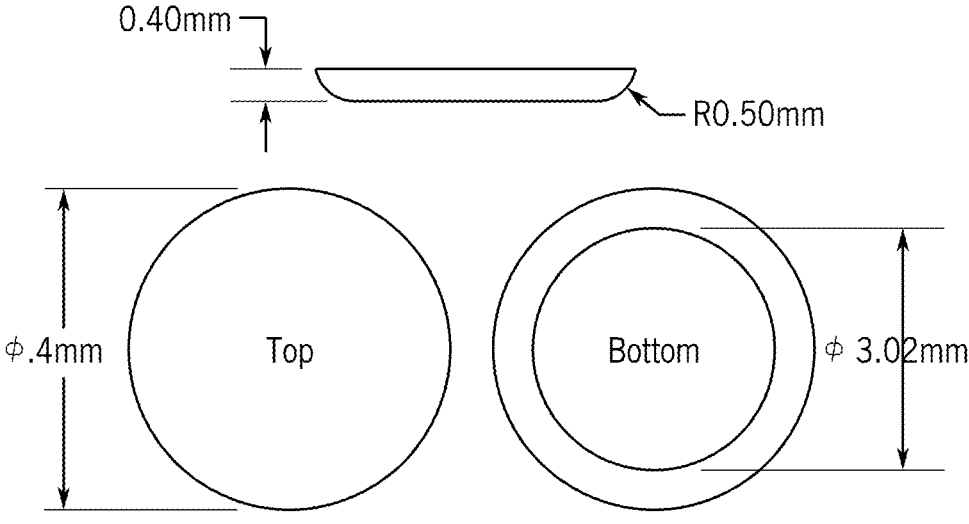
FIG. 2B shows one embodiment of the dimensions of the well and the lyophilized product prepared using the same.
Figure 2C:
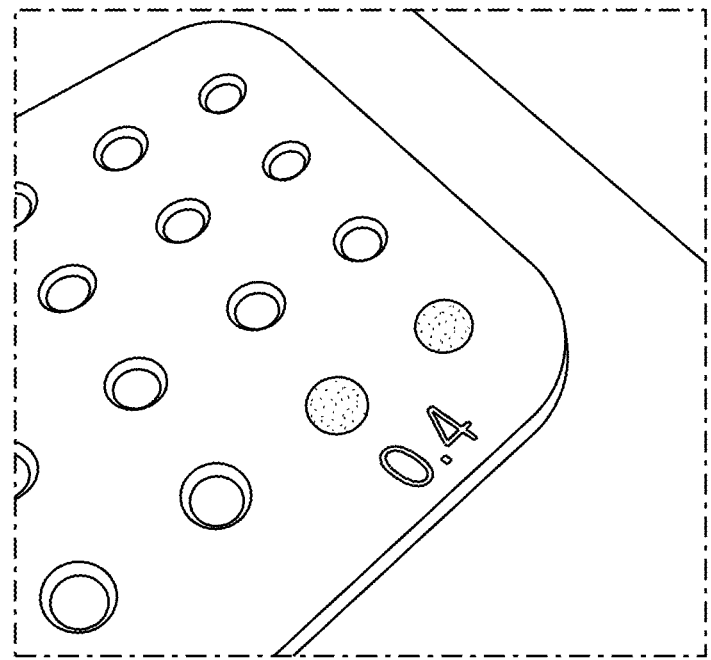
FIG. 2C shows a comparison of wells with and without coating. The well on the left was coated with hydrophilic coating, and the lyophilization mix covered the bottom of the well. The well on the right was not coated, and the lyophilization mix did not completely wet the bottom of the well.
Figure 3A:
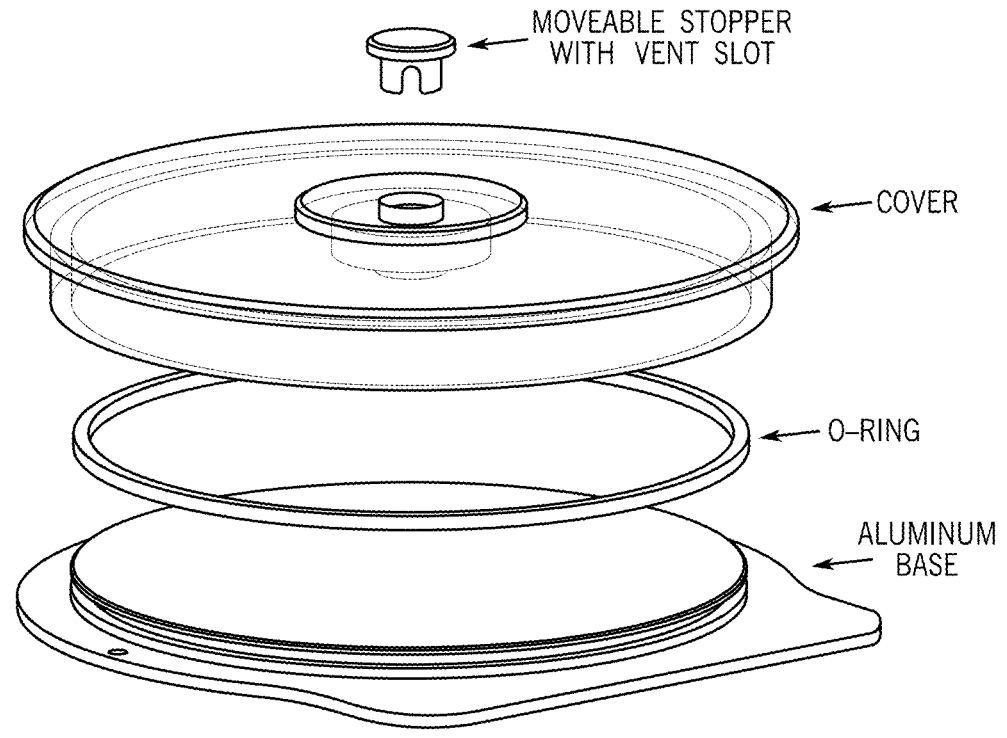
FIG. 3A-3E show various views of the lyo-saucer device, which may be used for lyophilization of a pellet atop a planar-topped column or within a well as described herein.
Figure 3B:
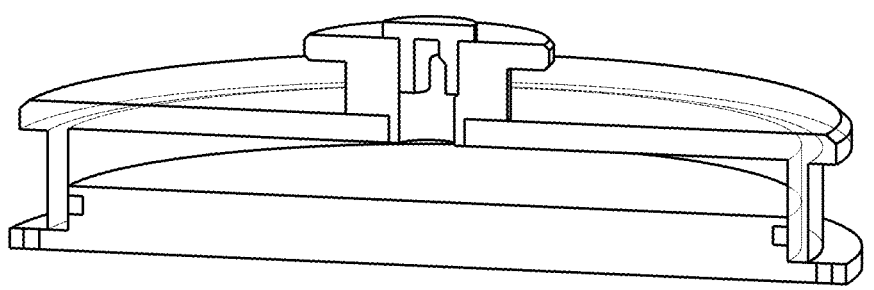
Figure 3C:
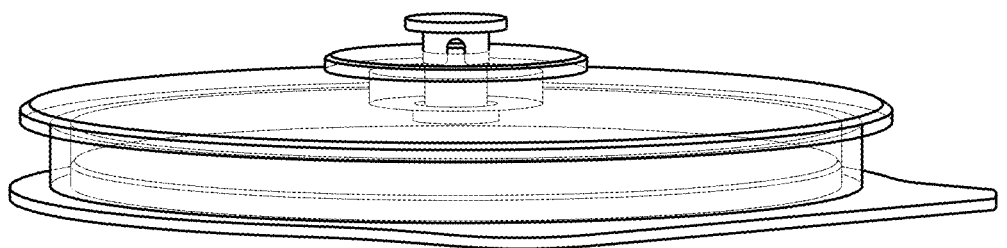
Figure 3D:
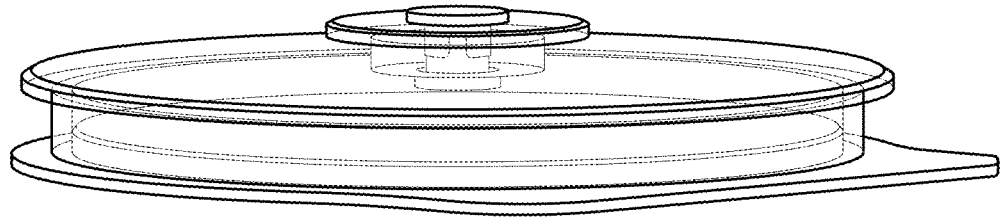
Figure 3E:
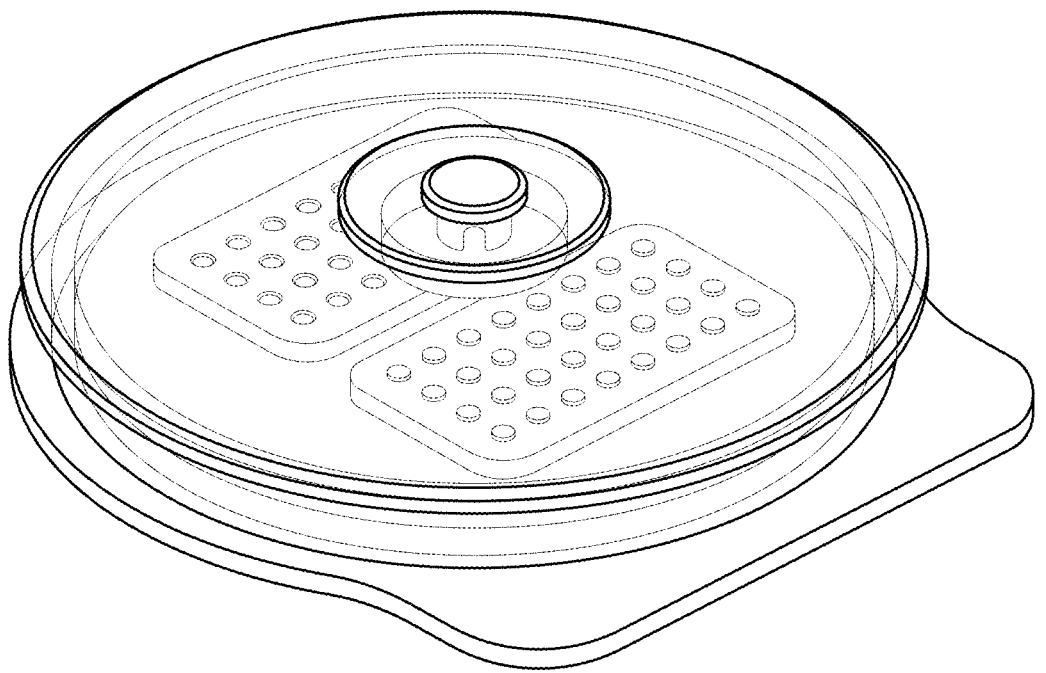

Disk formed in a well: An aluminum pan containing multiple wells (FIG. 2A) was chilled to approximately –1 to –2° C. The dimensions of the well are shown in FIG. 2B. 4.4 μL of a reagent mixture was pipetted into each well, using the pipette tip to guide the liquid to completely fill the well. In some embodiments, a hydrophilic coating compatible with lyophilization and PCR are used to coat the aluminum well to spread the liquid across the bottom of the well. As shown in FIG. 2C, when low volumes of reagents are used, the reagent mixture dispensed into wells does not reliably wet out the entire well without the aid of a hydrophilic coating. The well on the left was coated with hydrophilic coating, and the lyophilization mix covered the bottom of the well. The well on the right was not coated, and the lyophilization mix did not completely wet the bottom, and the lyophilized product does not have a uniform size and shape.

After dispensing the reagent mixture into the wells of the plate, the plate was transferred to the lyophilizer shelf pre-chilled to –45° C. for about 5 minutes to ensure freezing of the reagent mixture. Lyophilization was performed after freezing using the lyo-saucer. After lyophilization, the lyo-saucer was sealed with back filled $N_2$. The lyo-saucer was subsequently opened in the dry room by releasing $N_2$ slowly via piercing stopper with needle. In the dry room, the lyophilized pellets were moved from the plate to a cartridge using a vacuum pen. Adhesive fingers in the PCR chamber were used for placement of the disk. Unused disks were stored in tubes sealed in aluminum pouches with desiccant.

Example 3—Lyophilization of PCR Reagents

The methods described herein can be used to form lyophilized pellets comprising PCR reagents. In this example, each PCR reaction to be lyophilized consists of 340.9 mM Trehalose (Life Sciences, St Petersburg, FL), 1.4 mM dNTPs (Invitrogen, Carlsbad, CA), 40.9 μM each forward and reverse oligonucleotides (Integrated DNA Technologies, Coralville, IA), 1.7 µM fluorescently-labeled oligonucleotide probe (Integrated DNA Technologies), 0.1% Tween-20 (Thermo Fisher Scientific, Waltham, MA), 5.1 mg/ml bovine serum albumen (Invitrogen, Carlsbad, CA), 75 mg/ml dextran 40000 (Sigma Aldrich, St Louis, MO), and 12 units of Hawk Z05 Fast DNA polymerase (Roche Diagnostics, Basel, Switzerland).

A plate containing a plurality of planar-topped columns was used. A suitable volume of the PCR reagents (e.g. reagent mixture) was placed on the surface of each planar-topped column by methods as described herein. Reagents were frozen and lyophilized. The lyophilization conditions were as follows:

The lyo-saucer device was chilled to –45° C. with the vacuum engaged. The vacuum was released, the plate containing the reagent mixture was placed onto the lyo-saucer, covered with the lid, and the rubber stopper was placed. The vacuum was engaged. Pressure went down to 51 mTorr. The shelf ramps up to –35° C. at a rate of 3° C./min. The plate was held at this pressure and temperature for 14 hours. After 14 hours, the shelf ramps up to 30° C. at a rate of 2° C./min. The plate was held at this temperature for 6 hours. The lyo-saucer was sealed with back filled $N_2$.

Figure 4:
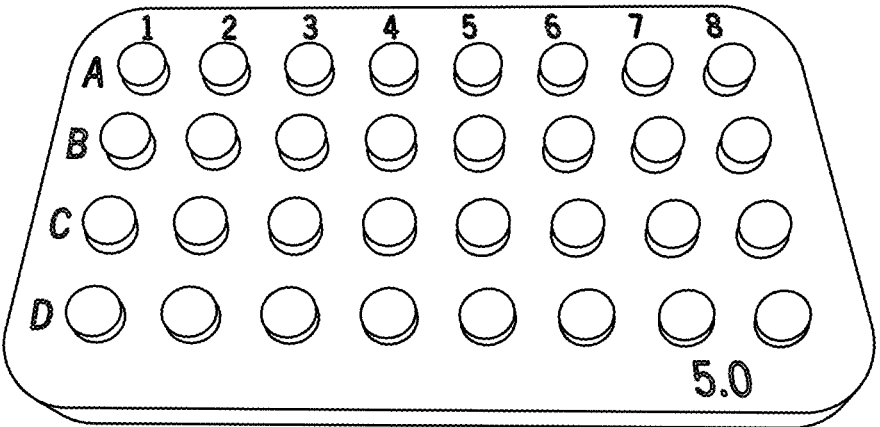
FIG. 4 shows a plate containing an array of planar-topped columns with lyophilized pellets with and without green dye.
Figure 5:
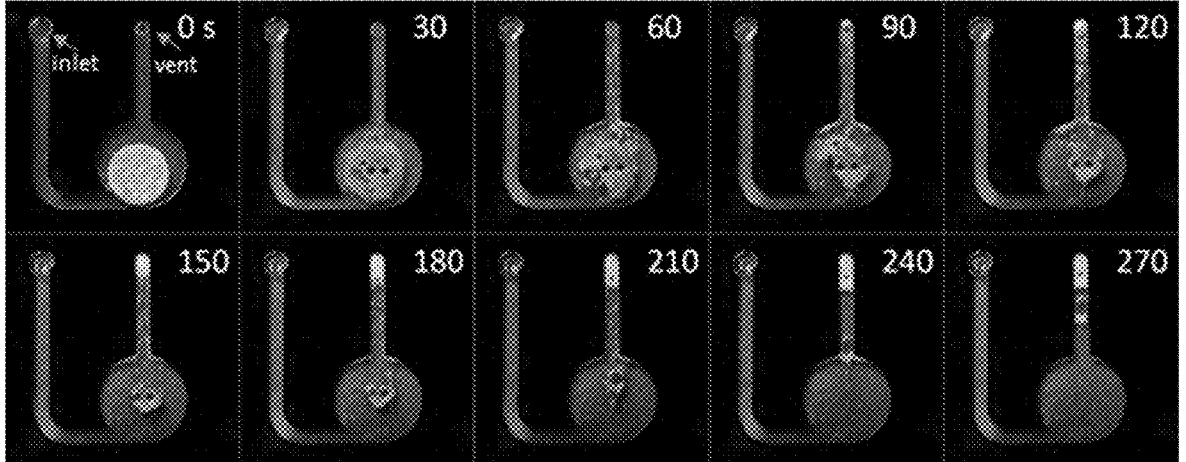
FIG. 5 shows rehydration of the lyophilized pellets from FIG. 4. Resuspension was performed in resuspension buffer.

Resuspension of PCR reagent in PCR chamber: Following lyophilization, pellets were resuspended in a PCR chamber. The lyophilized pellets were prepared on a planar-topped column with green dye for ease of observation. A plate containing an array of planar-topped columns with lyophilized pellets is shown in FIG. 4. Pellets were then placed in a FastPCR slide attached to 2 adhesive fingers to aid in positioning and to hold in place during shipment. Fifteen microliters of resuspension buffer were pipetted into slide in inlet. The pellet was resuspended and the entrapped air bubbles were allowed to rise out of the slide by a vent. Rehydrates are shown in FIG. 5.

Balance of Excipients: For lyophilization of PCR reagents, the balance of excipients (e.g. binding agents and bulking agents) may be useful for producing a superior product. IN particular, the lyophilized pellets produced herein satisfy the following characteristics:

1. Are pick-and-placeable for manufacturing (i.e. durable)
   i. Do not crack
   ii. Do not stick to freeze-drying protrusion/mold
2. Maintain enzyme activity during storage
3. Resuspend readily in resuspension buffer
4. Deliver active reagents for PCR with equivalent performance to freshly prepared ones
5. Have appropriate dimensions to fit into PCR chamber which is designed for optimal heat transfer—i.e. flat 0.4 mm h×4.6 mm D.

Of particular significance is the balance between rapid dissolution and the durability of the lyophilized pellet. Complete dissolution of the lyophilized reagent pellet is shown herein to occur in a timely manner in order for the reagents to be adequately mixed. From a solubility standpoint, it is desirable for the excipients to be present at the lowest concentration possible.

The pellets described herein are durable, such that they can be picked and placed during cartridge assembly without breaking. From a durability standpoint, it is desirable for the concentration of the excipients, i.e. the percent solids of the pellets, to be as high as possible without causing cracking of the pellet.

Additionally, the concentration of the excipients once dissolved in the PCR chamber have been considered herein, such that excipients do not interfere with accuracy of the PCR itself.

In some embodiments, the pellet comprises dextran as a binding agent and trehalose as a bulking agent. Accordingly, suitable concentrations of dextran and trehalose were tested herein. All concentrations of dextran in the PCR that were relevant for the other metrics were shown to be tolerated by PCR. Conversely, trehalose is a necessary crowding reagent that enhances PCR performance. The acceptable range of trehalose concentrations is also described herein. The acceptable range of trehalose is first dictated by PCR performance and then can be further narrowed down by the other metrics.

The levels of dextran and trehalose were selected by comparing 3 characteristics across a range of excipients (FIG. 7).

A range of hydrophilic polymers of different chemical compositions and molecular weights have been shown to be effective as binding agents. Accordingly, other suitable binding agents were tested (FIGS. 8A-8B). Solutions of dextran of 40,000 and 150,000 MW, polyvinylpyrrolidone of 40,000 MW, polyvinylalcohol of 30,000 MW, polyethylene glycol of 8,000 MW were tested at 5, 10 and 15% of lyophilized mix and lyophilized in depression plate (FIG. 7). Food coloring was added to make it easier to see the different pellets. The pellets were considered acceptable if they could be removed from depression plate with a vacuum pen without breaking apart. Hydroxyethylcellulose MW 90,000 and carboxymethylcellulose MW 90,000 were tested at lower concentrations of 1, 2 and 3% lyophilized mix solution because of their high viscosity.

Reagents tested via qPCR: To test the functionality of the lyophilized pellets for subsequent PCR, lyophilized reagents were prepared using the components shown in Table 1. Lyophilized products were subsequently reconstituted with resuspension buffer that contains the required buffers and salt for PCR, as shown in Table 2.

TABLE 1

| | Reaction Mixture | | |
|---|---|---|---|
| component | volume added per rxn (ul) | Concentration in 4.4 ul lyo mixture | Concentration in 15 ul resuspended PCR reaction |
| 1000 mM Trehalose | 1.5 | 340.9 | 100 |
| 25 mM dNTPs | 0.24 | 1.4 | 0.4 |
| 1000 uM F primer | 0.18 | 40.9 | 12.0 |
| 1000 uM R primer | 0.18 | 40.9 | 12.0 |
| 100 uM fluorescent probe | 0.075 | 1.7 | 0.5 |
| 10% Tween-20 | 0.044 | 0.1 | 0.03 |
| 50 mg/ml bovine serum albumen | 0.45 | 5.1 | 1.50 |
| 400 mg/ml dextran-40K | 0.825 | 75.0 | 22 |
| 200 U/ul Hawk Z05 Fast DNA polymerase | 0.06 | 2.7 | 0.8 |
| water | 0.85 | | |
| total | 4.4 | | |

15

TABLE 2

| Resuspension buffer components | |
| --- | --- |
| Resuspension buffer mix (stock conc.) conc. in PCR | per rxn |
| glycerol solution (60%) 10% | 2.5 |
| Tris pH = 8 (1M) 100 mM | 1.5 |
| bicine/KOH pH = 8.0 (1M) 62.4 mM | 0.936 |
| K-glutamate (3M) 65 mM | 0.325 |
| Tween-20 (0.2% total) | 0.26 |
| MgCl2 (100 mM) 4.0 mM | 0.6 |
| CT gDNA 1e4 copy/uL (6000 copies in 15 ul) | 0.6 |
| water | 8.28 |
| | 15.00 |

Figure 6:
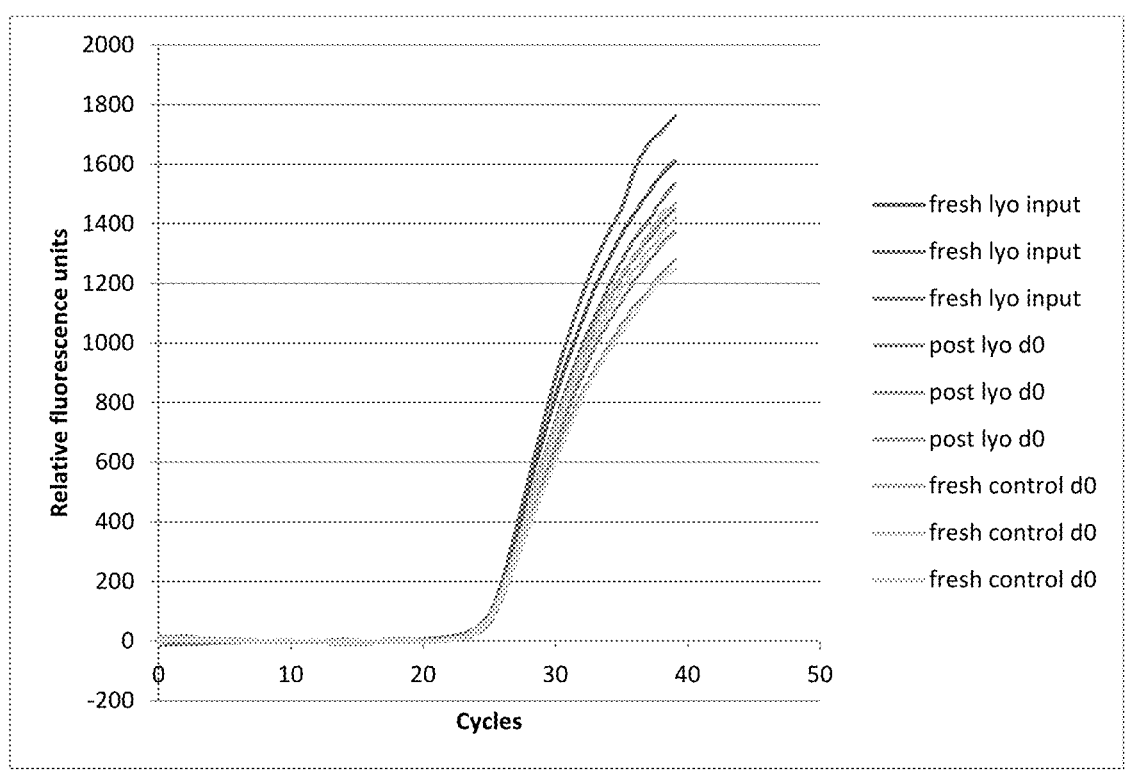
FIG. 6 shows quantitative PCR curves from rehydrated lyophilized pellets containing PCR reagents, with background subtracted.

The mixed reaction was then added to PCR mix with 6000 copies of *Chlamydia trachomatis* genomic DNA then dispensed into the PCR slide. Cycling parameters were: 15 seconds at 95° C.; 40 cycles of is at 95° C. followed by 4 s at 68° C. performed on M2Dx qPCR testbed and fluorescence was detected at every cycle. Results are shown in FIG. 6. For FIG. 6, "Fresh lyo input" was tested on the day of lyophilization to confirm that all constituents were included. After lyophilization was completed, the reagents were tested for performance ("post lyo d0"). A fresh mix was made that day as a comparator ("fresh control d0"). FIG. 6 shows quantitative PCR curves with background subtracted.

Data were analyzed by LinReg (http://LinRegPCR.nl) (Ramakers, Ruijter et al. 2003, Ruijter, Ramakers et al. 2009) to determine Cqs, and average Cq of all 3 conditions were essentially the same. Results are summarized in Table 3.

TABLE 3

| Summary of PCR Results | | | |
| --- | --- | --- | --- |
| Sample | Cq | Av. Cq | SD |
| 1_fresh_lyo_input | 24.51 | 24.76 | 0.23 |
| 2_fresh_lyo_input | 24.82 | | |
| 3_fresh_lyo_input | 24.95 | | |
| 4_post_lyo_d0 | 24.51 | 24.87 | 0.30 |

16

TABLE 3-continued

| Summary of PCR Results | | | |
| --- | --- | --- | --- |
| Sample | Cq | Av. Cq | SD |
| 5_post_lyo_d0 | 25.02 | | |
| 6_post_lyo_d0 | 25.07 | | |
| 7_fresh_control_d0 | 24.89 | 24.76 | 0.12 |
| 8_fresh_control_d0 | 24.73 | | |
| 9_fresh_control_d0 | 24.65 | | |

REFERENCES

Ramakers, C., et al. (2003). "Assumption-free analysis of quantitative real-time polymerase chain reaction (PCR) data." *Neurosci Lett* 339(1): 62-66.

Ruijter, J. M., et al. (2009). "Amplification efficiency: linking baseline and bias in the analysis of quantitative PCR data." *Nucleic Acids Res* 37(6): e45.

The invention claimed is:

1. A method of forming a circular pellet with a planar bottom and a domed top, comprising:
   (i) aligning a pipette containing a reagent mixture above a planar surface with a tip of the pipette at a non-vertical angle with respect to the planar surface, wherein the planar surface as been chilled to a temperature below a freezing temperature of the reagent mixture;
   (ii) dispensing a droplet of a reagent mixture from the pipette such that the droplet clings to the tip of the pipette; and
   (iii) adjusting the angle of the pipette tip to a vertical position such that the droplet falls from the tip onto the planar surface, such that the single droplet freezes upon contact with the planar surface.

2. The method of claim 1, wherein the planar surface comprises a metallic surface, an aluminum surface, or a glass surface.

3. The method of claim 1, wherein the droplet freezes within 1 second of contact with the planar surface.

4. The method of claim 1, wherein the reagent mixture comprises 6-8% dextran and 12-14% trehalose.

\* \* \* \* \*